United States Patent [19]

Thongpreda et al.

[11] Patent Number: 5,314,491
[45] Date of Patent: May 24, 1994

[54] PROSTHETIC SOCKET IMPLANT

[75] Inventors: Nisra Thongpreda; Fred Kline, both of Warsaw, Ind.

[73] Assignee: Zimmer, Inc., Warsaw, Ind.

[21] Appl. No.: 37,490

[22] Filed: Mar. 22, 1993

Related U.S. Application Data

[63] Continuation of Ser. No. 799,697, Nov. 25, 1991, abandoned, which is a continuation of Ser. No. 474,437, Feb. 2, 1990, abandoned.

[51] Int. Cl.⁵ ............................................... A61F 2/34
[52] U.S. Cl. ...................................................... 623/22
[58] Field of Search ........................ 623/16, 18, 19, 22, 623/23

[56] References Cited

U.S. PATENT DOCUMENTS

| | | | |
|---|---|---|---|
| 4,380,090 | 4/1983 | Ramos | 623/22 |
| 4,695,282 | 9/1987 | Forte et al. | 623/22 |
| 4,770,658 | 9/1988 | Garamakis | 623/22 |
| 5,019,105 | 5/1991 | Wiley | 623/23 |
| 5,062,853 | 11/1991 | Fortz | 623/22 |

FOREIGN PATENT DOCUMENTS

6065482  11/1982  European Pat. Off. ............. 623/22

*Primary Examiner*—David Isabella
*Attorney, Agent, or Firm*—Todd A. Dawson

[57] ABSTRACT

An improved socket for use in ball-and-socket joints, the socket including an outer shell and an inner low-friction bearing insert for mateable engagement with the head or ball-end of an associated component. The socket is suitable for prosthetic as well as non-prosthetic applications. The bearing insert is retained within the outer shell by a split, insert-retaining ring. The head of the associated component is retained within a spherical chamber within the bearing insert by a split annular bearing ring carried by and mated with annularly spaced apertures in the insert. Assembly of the device by inserting the head of the associated component causes expansion of the bearing ring to receive the head and the subsequent insertion of the bearing insert into the outer shell locks the head in place. Radially outwardly extending arcuate tabs on the bearing ring bear against the inner surface of the outer shell to thereby oppose expansion of the bearing ring after the device is assembled. The ends of the insert-retaining ring are accessible through an aperture in the outer shell to enable disassembly of the components.

12 Claims, 5 Drawing Sheets

PROSTHETIC SOCKET IMPLANT

This application is a continuation of application Ser. No. 07/799,697 filed Nov. 25, 1991, now abandoned which is a continuation of application Ser. No. 07/474,437 filed Feb. 2, 1990, now abandoned.

BACKGROUND OF THE INVENTION

1. Field of the Invention

This invention relates generally to ball-and-socket joints and, in particular, to implantable prostheses. More particularly, the invention relates to an implantable prosthetic socket having a bearing insert interposed between the spherical head of an associated prosthetic component and the socket component of the prosthesis.

2. Description of the Prior Art

Joint replacements—total and partial—have in recent years become reliable orthopedic procedures for the correction of disorders of natural joints. These procedures when applied to a hip joint, for example, involve the surgical implantation of a femoral stem prosthesis into the femur and an acetabular endoprosthesis into the acetabulum for receiving the femoral head. Similar procedures and components may be used with other ball-and-socket type joints such as, for example, a shoulder joint, although the preferred embodiment disclosed herein is described in terms of a hip joint. Additionally, while the preferred embodiment is described in terms of an implantable prosthetic socket, those skilled in the art will understand that the invention may be applied to ball-and-socket joints in general, whether intended to be implantable or not and indeed may be applied to other than "spherical" ball-and-socket joints.

Numerous devices have been developed in an effort to produce a prosthetic hip implant which is not only easy to implant or remove, if necessary, but which also approximates as closely as possible the performance of the natural joint. While all known devices have a femoral and an acetabular component, the design of the latter varies widely depending upon the dysfunction being corrected. The acetabular socket component is generally a biocompatible metallic member that may, for example, be either movably or immovably secured into the acetabulum. In either case, the acetabular socket has a low-friction biocompatible bearing insert (generally polyethylene) with a seat or socket chamber for receiving the spherical head or ball-end of the femoral component.

Those devices which have a fixed acetabular component have a rigid, cup-shaped socket component intended to be retained within the natural acetabular socket. They have a single articulating surface—that is, the head of the femoral component is movable within the bearing insert. Another class of devices is known wherein the acetabular socket component is movable within the natural socket. These devices have a rigid, cup-shaped outer shell with a highly polished outer spherical surface designed to move within the natural socket. These devices have two articulating surfaces—the head and the outer surface of the socket—and are generally known as "bipolar", including both concentric and non-concentric designs, the latter having varying degrees of eccentricity or polar offset.

An important consideration in the design of bipolar hip endoprostheses is enhancement of the prosthesis to resist the tendency of the acetabular cup of these implants to rotate toward varus. Producing bipolar endoprostheses with an antivarus property (i.e. polar offset) is desirable in order to advantageously distribute the inherent forces which tend to deform the implant's components and, in the extreme, result in dislocation. The general manner in which an antivarus property is effected is by providing a polar offset. Ball-and-socket type joints are subject to dislocation under a certain types or amounts of stress and producing these joints (for hip applications) with a polar offset between the inner and outer articulating components tends to decrease these stresses, thereby decreasing the tendency of these components to come apart. It is a goal of all ball-and-socket type prostheses to overcome this tendency by more securely capturing the femoral head within the bearing insert. It is a particular object of this invention to provide a socket which strongly captures the femoral head over a wide range of polar offsets (to accomodate prostheses of various sizes).

The importance of securely capturing the head in a socket must be considered in the light of other desirable factors such as ease of assembly and installation and ease of disassembly. Occasionally, due to subsequent injury or disease, the replacement of all or part of the prosthesis becomes necessary. Consequently, while such devices are often designed with the intention of separating the various components if necessary, simultaneous consideration must be given to making sure the assembled components do not easily become separated during normal use. Numerous prior art devices are known which disclose many ways of accomodating ease of assembly, resistance to dislocation and ease of disassembly in prosthetic ball-and-socket joints.

U.S. Pat. No. 3,813,699 (Giliberty) discloses an outer shell with a bearing insert immovably secured to the shell. The insert has a constricted opening and is of a resilient silicone material capable of yielding sufficiently to enable the head of the femoral stem prosthesis to be inserted into the socket of the insert while thereafter capable of retaining the head in an articulating manner.

U.S. Pat. No. 3,818,512 (Shersher) discloses a prosthesis having a conventional, fixed acetabular component. The device includes an outer metal shell and a bearing insert having a plurality of fingers or leaves intended to be compressed inwardly to retain the head of the femoral component. The compression is achieved by a self-locking nut which threads into the outer metal shell, the inner surface of the nut being shaped to conform to the fingers of the bearing insert. The nut has several lugs to facilitate the threading of the nut into the acetabular component and is locked to the outer shell by a partial circumferential slot splitting the nut into two parallel parts which are then compressed together by a screw. While the Shersher device includes a locking element to more positively secure the head of the femoral prosthesis to the acetabular shell, this locking mechanism—even if it were adapted for use in a bipolar prosthesis—is difficult to use in practice because of the required threaded motion.

U.S. Pat. No. 3,863,273 (Averill) discloses a similar type of locking or capture mechanism to secure the head of the femoral component into the bearing insert. The bearing insert of Averill is secured within the outer shell by a radially outwardly extending tab on the insert snapping into a corresponding annular groove on the inner wall of the outer shell. The open end of the bearing insert is a greatly constricted opening having longitudinal slots defining fingers which are radially expanded to enlarge the opening when the head is pushed in. The Averill device relies only on the tension of the fingers to hold the femoral head, the fingers being supported by the surrounding inner surface of the outer shell, and does not disclose any other positive locking mechanism to secure the head of the femoral component within the bearing insert. As will be understood by those skilled in the art, this structure and other similar types of structures described below necessarily require a large amount of plastic bearing insert material between the head and the opening of the metal shell. This contributes to deformation of the bearing insert and subsequent dislocation under high loads. The Averill device does not disclose any specific means for disassembling the femoral head from the bearing insert.

U.S. Pat. No. 4,784,663 (Kenna) discloses a structure similar to Averill except that the resilient fingers or leaves of the bearing insert are prevented from expanding radially outwardly by a polyethylene locking ring interposed between the open end of the bearing insert and the open end of the outer shell and retained in place by the cooperative action of an annular rib and groove attaching mechanism. The Kenna device facilitates disassembly by having an annular gap between the lip of the locking ring and the adjacent periphery of the metal shell. The locking ring may be pulled apart from the bearing insert by prying the lip away from the shell periphery using a suitable tool inserted in the annular gap.

U.S. Pat. No. 4,770,658 (Geremakis) discloses another type of locking ring in a joint prosthesis. In this device a bearing insert is provided with a plurality of axially extending fingers designed to be pressed radially inwardly by a lock ring interposed between the fingers and the outer metal shell. The lock ring is carried by the outer shell in a first position enabling the insertion of the head of an associated component and a second position in which the lock ring tightly engages the bearing insert and the outer shell to maintain the bearing insert in overlapping relation to the head. Unlocking is achieved by pulling the lock ring axially away from the outer shell (a part of the rim of the shell is cut-out for this purpose).

U.S. Pat. No. 4,241,463 (Khovaylo) discloses a prosthetic hip implant wherein the femoral head is captured within the spherical cavity of a bearing insert by a split polyethylene retaining ring as opposed to a solid ring, the ring being interposed between the head and the inside of the insert (rather than the inside of the outer shell). The insert is keyed to prevent its rotation relative to the outer shell and the split ring is adapted to move within a cavity of the bearing insert within a limited axial range. Upon insertion of the femoral head into the bearing insert, the split ring is forced axially to one extreme end of its axial range of motion where the cavity is larger so the ring may expand radially to enable it to open up sufficiently to permit the head to enter the spherical seat of the insert. When the head is properly seated, it clears the split ring sufficiently to enable the ring to return to its normal size underneath the femoral head. The interior cavity of the bearing insert and the split ring are so angled that attempted removal of the femoral head tends to wedge the split ring against the interior of the bearing insert thereby preventing removal of the femoral head under normal circumstances. A slot is provided adjacent the opening of the bearing insert to enable a tool to be inserted in order to push the split ring inwardly to its expanded position in order to enable the femoral head to be removed.

U.S. Pat. No. 4,380,090 (Ramos) discloses a hip prosthesis with a split annular polyethylene bearing similar to Khovaylo, but adjacent the open end of a bearing insert between the head and the outer shell. The split bearing is retained by split metal locking ring held within an inner annular groove on the outer shell. Removal of the bearing insert is accomplished by compressing the metal locking ring to remove it, the bearing insert and the split annular bearing.

U.S. Pat. No. 4,619,658 (Pappas et al.) discloses various prosthetic hip implants, some having solid bearing rings and some having split bearing rings. In one embodiment, the body of the bearing insert is formed from a plurality of segments (split in a plane passing through and parallel to the axis) which are held together by a circular retaining ring and which are held within an outer metal shell by the cooperative action of the retaining ring with a groove on the inner surface of the outer shell. In another embodiment, the bearing insert is formed of two pieces split along a transverse plane: a primary bearing insert forming the major part of the spherical head of the insert and a split collar (i.e. bearing ring) for being attached to the open end of the primary bearing insert. The collar and the primary bearing insert are held together by the interaction of cooperative annular ribs and grooves and the assembly is then inserted into an outer metal shell. A substantially circular release tool may be inserted into the open end of the outer shell between it and the bearing insert to compress the ring of the first embodiment to remove the bearing insert from the outer metal shell. In the second embodiment the collar may be provided with holes or slots into which the ends of conventional clamps may be inserted to squeeze the collar together thereby reducing its circumference at the radial split in order to enable the bearing insert to be removed from the outer shell.

U.S. Pat. No. 4,714,477 (Fichera et al.) discloses another version of a split bearing ring in a single-piece bearing insert having an upper circumferential portion and a lower portion integrally connected to the upper portion but separated from it by a circumferential split (extending less than 360°). The lower portion itself is split along a vertical line and is retained within the outer shell by an annular rib engaged within an annular groove of the shell.

All known ball-and-socket devices appear to suffer from the inherent limitation that, under extreme ranges of motion where the loads may be expected to be greatest, plastic flow may occur in the bearing insert (and other plastic components). This is especially true of those implantable devices subject to rotate toward varus so that the forces tend to be directed against the rim of the cup and insert. Even in embodiments which may not be subject to rotation toward varus (as in, for example, non-implanted joints) the forces causing dislocation of the head from the spherical cavity are, in many prior art designs, directed primarily against that portion of the bearing insert and/or bearing ring adjacent the open end of the outer cup. That is, the forces are directed against a portion of the bearing insert which is not supported by much more than the plastic mass of the bearing insert itself. Increasing the mass of bearing insert material has not been of any particular advantage in increasing the resistance of the prior art sockets to dislocation.

It is accordingly an object of this invention to produce an improved socket for use in ball-and-socket joints to provide increased resistance to dislocation.

It is another object of this invention to produce an implantable prosthetic socket wherein the head of an associated femoral stem prosthesis is captured within the socket of a bearing insert by a substantially annular bearing ring.

It is a further object of this invention to produce an implantable prosthetic socket joint capable of being easily assembled and disassembled. It is in part an object of this invention to facilitate the assembly and disassembly operations by minimizing the number of components and subassemblies required to produce an operational prosthetic joint.

It is yet another object of this invention to produce an implantable prosthetic socket having an outer shell and an inner bearing insert and utilizing a split bearing ring to form part of the socket chamber within the bearing insert, the prosthetic socket adapted to have the split bearing ring being directly in contact with both the head of an associated prosthetic component and the inner surface of the outer shell along an interior portion thereof distal from the opening.

It is also an object of this invention to produce a unique bipolar endoprosthesis adaptable to a range of eccentricities while also maximizing the ability of the assembled components to resist dislocation.

SUMMARY OF THE INVENTION

These and other objects of the invention are achieved by the preferred embodiment disclosed herein which is a socket comprising an outer shell, a bearing insert disposed within the outer shell and defining a cavity for receiving a head to be coupled with the socket, a first means cooperating with the outer shell and the bearing insert to oppose separation therebetween, and a second means spaced from the first means and contiguously cooperating with the head, bearing insert and outer shell to oppose withdrawal of the head from the bearing insert. The second means may be an annular split ring carried in a plurality of apertures extending through the wall of the insert and being shaped to provide part of the surface of the cavity receiving the head while simultaneously being contiguous to the inner surface of the outer shell.

A particular embodiment of the invention comprises: an outer, cup-shaped shell provided with an interior chamber, one end of which defines the open end of said outer shell, said outer shell having a first annular groove formed on its inner surface proximate said open end and further having an access aperture therethrough, said aperture superimposed on said first groove; a cup-shaped bearing insert having an inner surface defining a socket chamber for receiving a head and an outer surface adapted for substantially mateable engagement within said outer shell, said outer surface having a second annular second groove proximate the open end thereof and a plurality of annularly spaced apertures axially spaced from said second groove; a split, insert-retaining ring adapted to fit within said first and second grooves, said insert-retaining ring provided with grasping means adjacent each end thereof, said grasping means accessible through said access aperture from the exterior of said outer shell to enable expansion of the normal radius of said insert-retaining ring; a split, head-retaining bearing ring retained within said spaced apertures of said bearing insert, said bearing ring being sufficiently radially expandable through said spaced apertures, when said bearing insert is not within said outer shell, to enable said head to be inserted past same into the socket chamber of said bearing insert, the outer diameter of said bearing ring being substantially equal to the inner diameter of said outer shell such that the expansion of said bearing ring is limited by said outer shell to oppose disengagement of said head from said bearing insert.

DESCRIPTION OF THE PREFERRED EMBODIMENT

Figure 1:
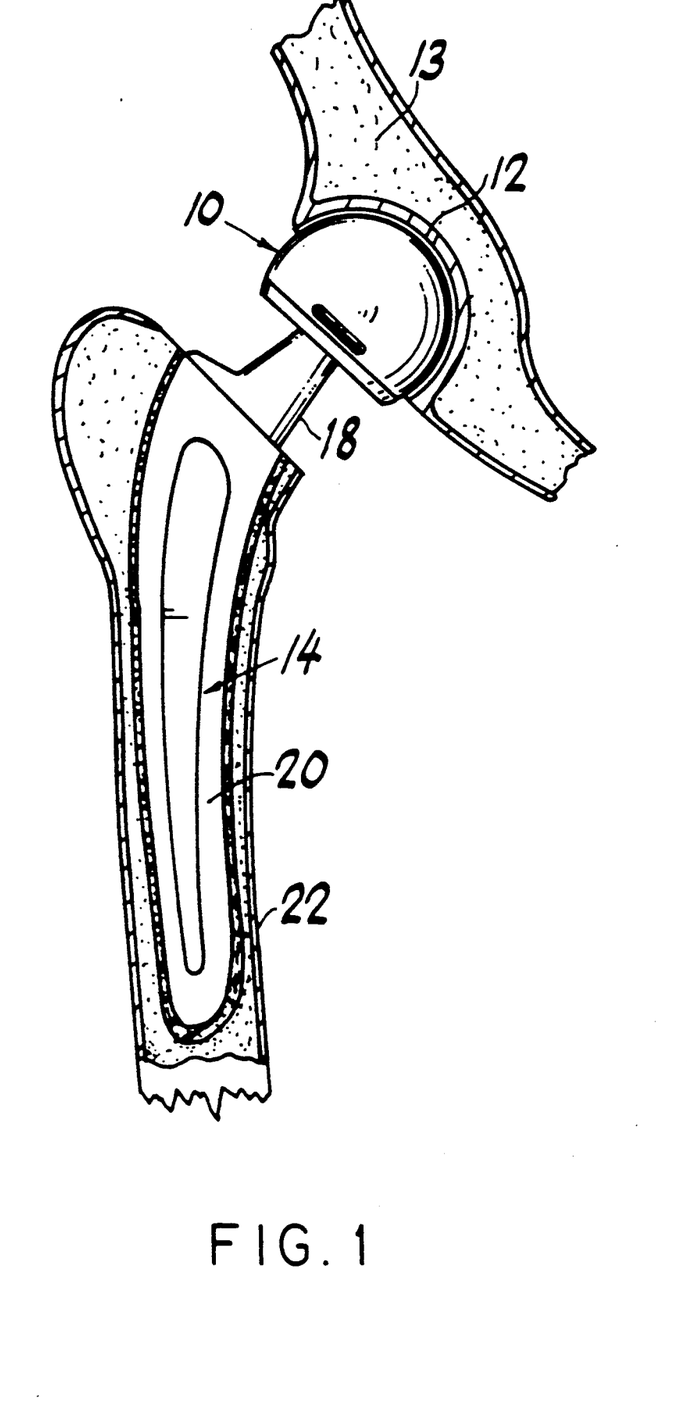
FIG. 1 is a diagrammatic elevational view of a preferred embodiment of an implantable prosthetic form of the invention illustrating a position of the prosthetic device in a patient.

Referring now to FIG. 1, the preferred embodiment of the invention is shown in the form of a prosthetic hip joint comprising an acetabular endoprosthesis 10 intended to be implanted into the natural acetabular socket 12 of a patient's acetabulum 13 and also intended to be used with a conventional femoral stem prosthesis or component 14 to provide substantially universal articulation. Any one of a variety of femoral components may be used provided they each have at their proximal ends a substantially spherical head 16 (best seen in FIG. 2) shaped and sized to mate within a substantially spherical cavity within acetabular endoprosthesis 10. Head 16 of the femoral component 14 is secured by neck 18 to stem 20 which is implanted within the intramedullary canal of femur 22 in a conventional manner.

Figure 2:
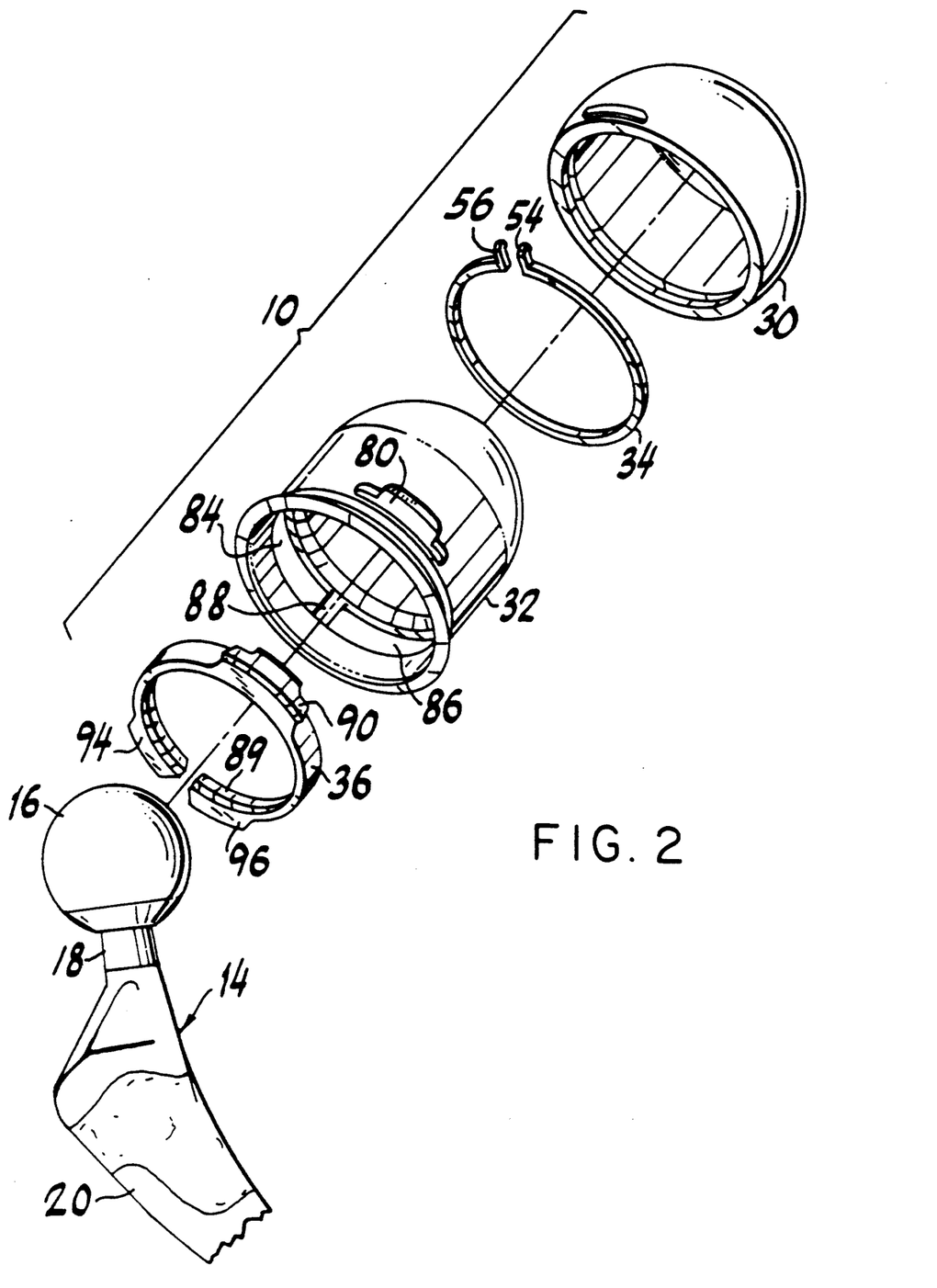
FIG. 2 is an exploded perspective view of the preferred embodiment of FIG. 1.

Acetabular endoprosthesis 10 comprises four discrete subcomponents: outer shell 30, inner liner or bearing insert 32, split insert-retaining or locking ring 34 interposed between the outer shell and the bearing insert and split annular bearing ring 36 interposed between the bearing insert and the associated head 16 of the femoral component. In an implantable embodiment of the invention outer shell 30 and locking ring 34 should be made of rigid, for example, metallic biocompatible components and bearing insert 32 and bearing ring 36 should be made of a biocompatible low-friction material. In the preferred embodiment, outer shell 30 is made of a cobalt-chromium-molybdenum alloy, bearing insert 32 and bearing ring 36 are made of an ultra-high molecular weight polyethylene and locking ring 34 is made of a titanium alloy.

Figure 3:
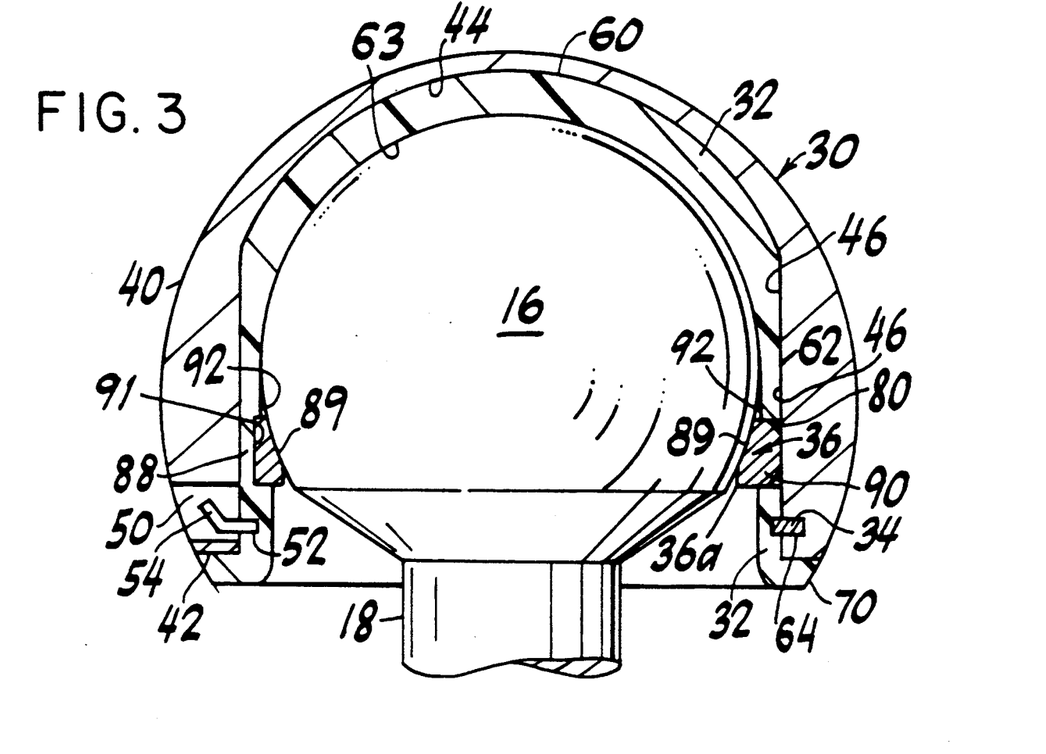
FIG. 3 is a cross-sectional view of a portion of the preferred embodiment of FIG. 1, a portion of FIG. 3 being exploded in scale.
Figure 7:
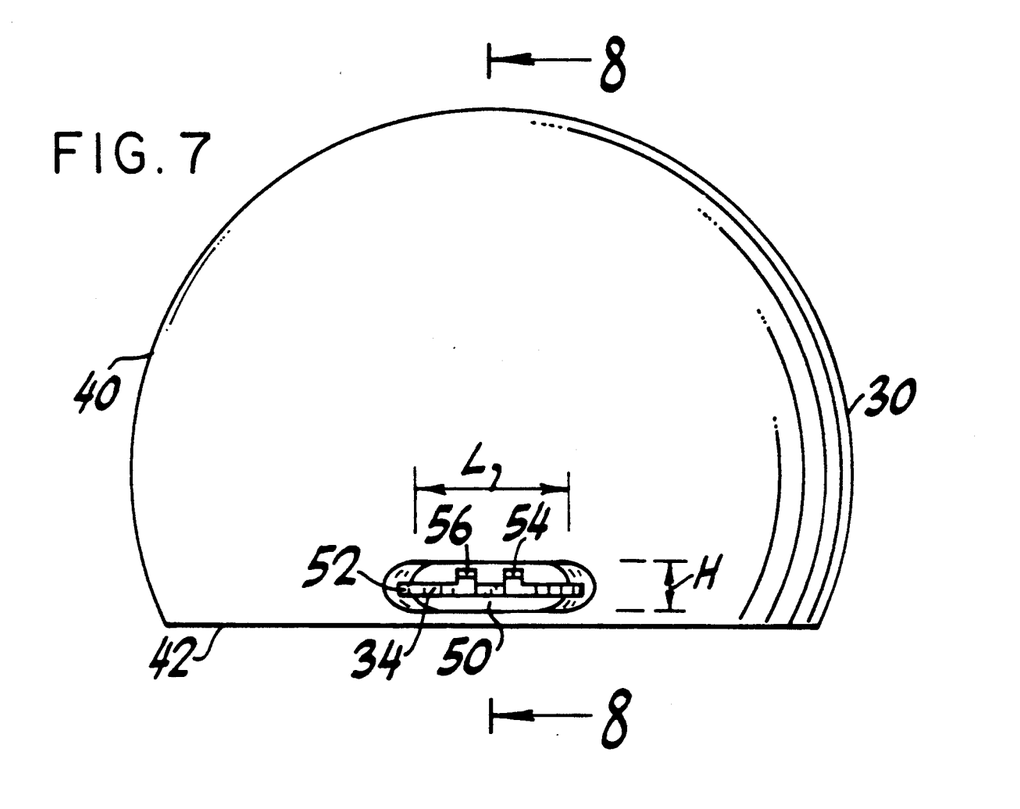
FIG. 7 is an elevational view of a portion of the invention.
Figure 8:
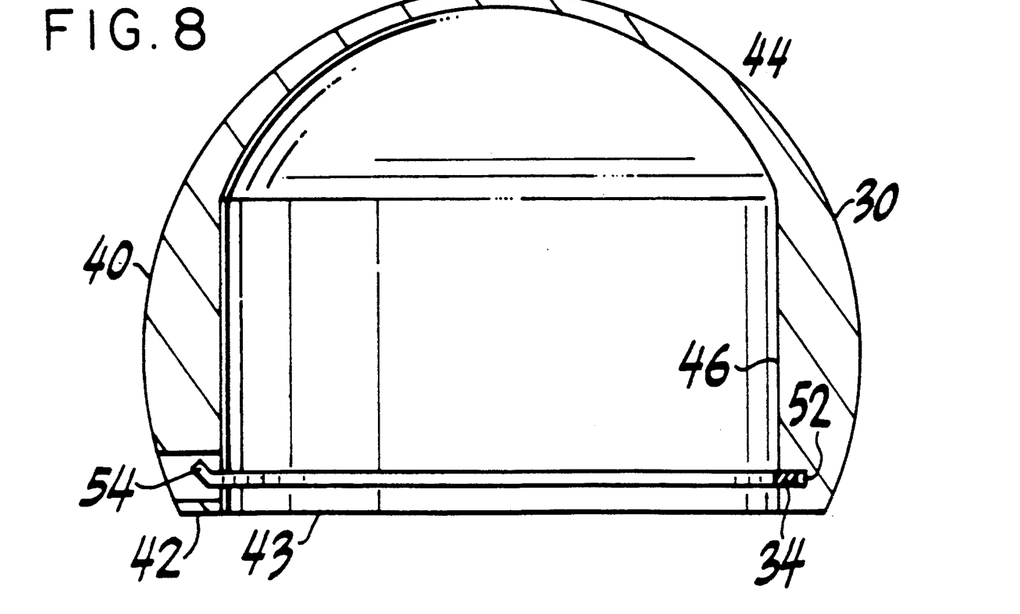
FIG. 8 is a cross-sectional view of FIG. 7 taken along the lines 8—8.

The exploded components of FIG. 2 are shown assembled in FIG. 3 in cross-section. Referring to FIGS. 3, 7 and 8, it will be noted that outer shell 30 is a generally cup-shaped structure having a highly polished spherical outer surface 40 terminating in a planar rim 42 around an open end 43. The inner surface of outer shell 30 has an axially symmetrical, spherically shaped inner wall 44 merging with an axially symmetrical, cylindrically shaped inner wall 46. Outer shell 30 is provided with a small, generally arcuate access aperture or slot 50 having a predetermined height H and arcuate length L (the latter being measured on the inner surface and the lateral edges of aperture 50 being radially extending). The angle subtended by length L may vary with the outer diameter of shell 30 to accomodate different size implants. Inner surface 46 is provided with a peripheral groove 52 situated at a level so that groove 52 will intersect aperture 50. In the preferred embodiment, since a spherical ball-and-socket joint is disclosed and the outer shell is spherical, the peripheral groove is annular. As discussed below, some embodiments of the invention may be shaped differently in which case the groove and other components described herein may be other than annular. Groove 52 is provided with a sufficient outer diameter and sufficient height to accomodate locking ring 34 which, in the preferred embodiment, has a rectangular cross-section. In order to make locking ring 34 releasable, the spaced ends of the ring are provided with grasping members 54 and 56 which are accessible from the exterior of outer shell 30 via aperture 50. While grasping members 54 and 56 are radially outwardly extending and are shown as upturned tabs, any suitably shaped ends or other means may be used so that the ends may be grasped or pushed apart with an associated tool (not shown). As will be understood below, the inner diameter of locking ring 34 is adapted to mate within a corresponding groove 64 within the outer surface of bearing insert 32 in order to retain the bearing insert within outer shell 30.

Figure 4:
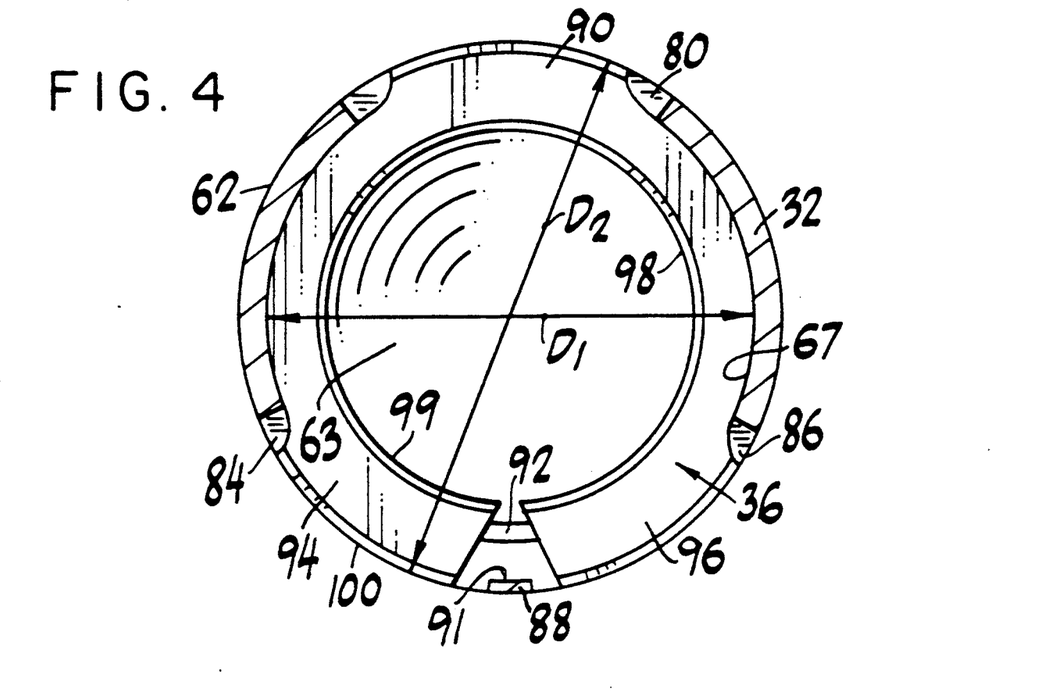
FIG. 4 is a cross-sectional view of a portion of the preferred embodiment as taken along the line 4—4 of FIG. 5.
Figure 5:
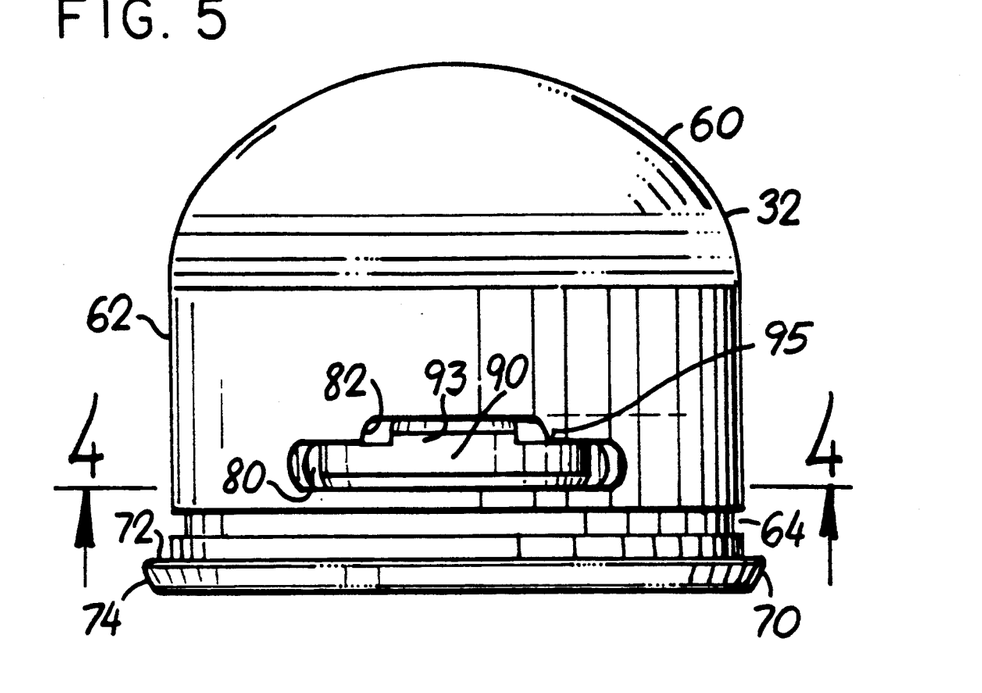
FIG. 5 is an elevational view of the bearing insert of the preferred embodiment of FIG. 1.
Figure 6:
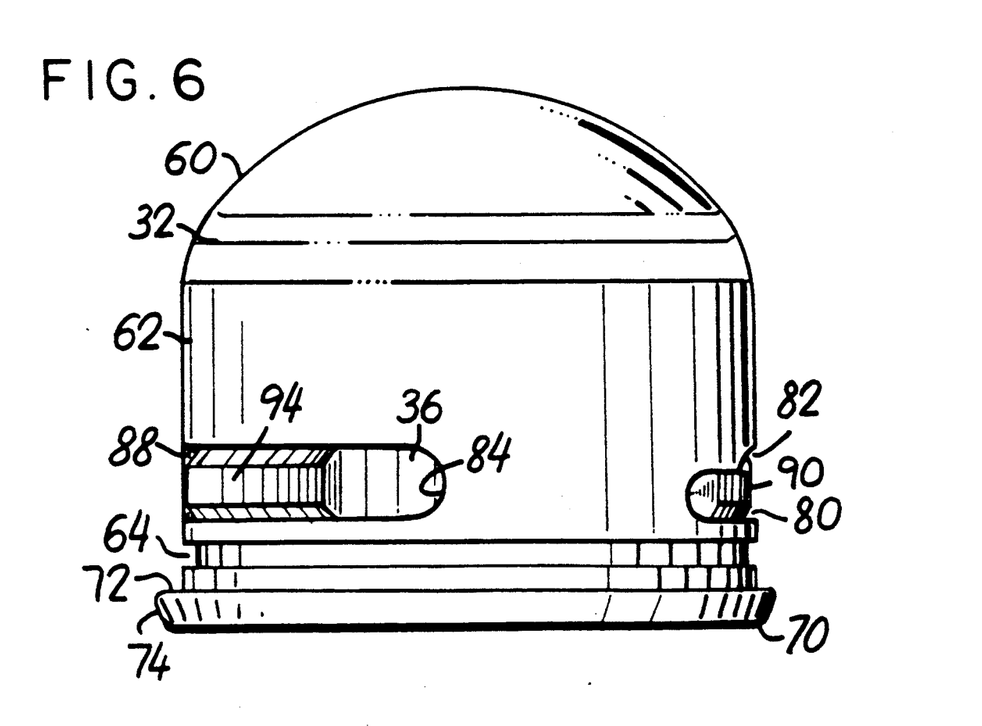
FIG. 6 is a left end elevational view of FIG. 5.

Bearing insert 32, best seen in FIGS. 4, 5 and 6, has an external axially symmetrical spherical surface 60 and cylindrical surface 62, both shaped to conform to the inner surfaces 44, 46 of outer shell 30. Insert 32 has an open end surrounded by an annular flange 70 having an annular shoulder 72 for contiguous engagement against planar rim 42 when insert 32 is engaged with outer shell 30. Flange 70 has a portion of a spherical surface 74 designed to smoothly blend into the spherical surface 40 of outer shell 30. It will be understood that the thickness of the spherical and cylindrical walls of bearing insert 32 is dependent upon the relative sizes of the acetabular shell 30 and femoral head 16 being used in any particular patient. Nevertheless, in all cases insert 32 is provided with a plurality of arcuate apertures 80, 84 and 86 to receive bearing ring 36.

Inner cylindrical wall 67 is also provided with annular groove 91 having a height or axial length sufficient to receive bearing ring 36. Groove 91 assists in retaining the bearing ring in the bearing subassembly (discussed below) and may be quite shallow in some sizes and relatively deep in others. Arcuate apertures 84 and 86 may be arcuately enlarged (even beyond 90°) as the bearing insert wall thickness increases to enable proper flexing of the bearing ring during assembly. A slight annular chamfer 92 is provided above groove 91 to prevent any interference upon insertion of head 16. The lower portion of insert 32 (below ring 36) may also be tapered outwardly in some applications to enhance the range of motion of the joint. In the preferred embodiment, one of the apertures, 80, is a keyed aperture having a predetermined arcuate length and a slightly axially enlarged and arcuately shortened key receiving portion 82. Apertures 84 and 86 each have a predetermined arcuate length (not necessarily the same as that of aperture 80) and are generally diametrically and symmetrically disposed relative to keyed aperture 80. Apertures 84 and 86 may be separated by a small section 88 of the cylindrical wall of the insert which helps to retain the ring in the bearing subassembly and provides additional strength to the wall of the bearing insert. Bearing insert 32 has an inner spherical surface 63 which serves as a seat for head 16 in conjunction with the seat portion of bearing ring 36.

Bearing ring 36, best seen in FIGS. 2, 3 and 4, is shaped to fit within outer shell 30 as well as to conform to apertures 80, 84 and 86 and to femoral head 16. Ring 36 has an annular seat 89 (save for the split) and, as best seen in FIG. 4, includes chamfered arcuate projections or tabs 90, 94 and 96 intended to mate with corresponding apertures 80, 84 and 86, respectively. Groove 64, aperture 50 and ring 34 are intended to be distal to apertures 80, 84 and 86 and as close to open end 43 as possible in order not to interfere with the articulation of the outer surface of shell 30. Obviously, for the same reason, grasping members 54 and 56 should not extend beyond surface 40. The tabs and the bearing ring are shaped and sized so that, when acetabular endoprosthesis 10 is operatively assembled with an associated head, bearing ring 36 will conform to the inner surface of shell 30 and head 16 such that (as best seen in the exploded part of FIG. 3) the ring will be simultaneously contiguous to the head (via seat 89), inner surface 46 (via tabs 90, 94 and 96) and to the bearing insert itself (via the overlying contact between the sides of the bearing ring with the sides of apertures 80, 84 and 86). An inner chamfered edge 36a of ring 36 may be provided to facilitate assembly.

It will be noted that bearing ring 36 has, in its normal relaxed configuration, a diameter $D_1$ measured across the main body of ring 36 and a diameter $D_2$ measured across the most radially outward parts of tabs 90, 94 and 96. Diameter $D_1$ is substantially equal to the inner diameter of the inner cylindrical surface 67 of bearing insert 32, while diameter $D_2$ is substantially equal to the inner diameter of inner cylindrical surface 46 of outer shell 30. Consequently, it will be understood that apertures 80, 84 and 86 must have a sufficient arcuate length to enable at least some of the tabs to expand radially therethrough when a femoral head is being forced past ring 36. Each tab 94 and 96 has a height substantially equal to that of the bearing ring and of its corresponding aperture 84 and 86, respectively. While the bearing ring may be provided with a range of diameters to accomodate different size implants, the height of the various rings may be similar. The keyed tab 90, as best seen in FIG. 5, has a short axially directed and arcuately extending key extension 93 adapted to fit within key aperture portion 82. Because the height of tab 90 together with extension 91 is substantially that of ring 36, key extension 91 is bounded on either side by the bearing ring body itself. Therefore, in the area marked 95, the bearing ring body overlaps with the bearing insert's inner cylindrical wall 67 to provide additional radial support to the bearing ring. Bearing ring 36 must be formed of a material sufficiently smooth and hard to provide a low-friction bearing surface but it must be designed to be sufficiently expandable to enable head 16 to be forced through the ring's normal circular opening 98. The preferred embodiment achieves this by providing a transverse split in ring 36. It is desirable to have a smaller gap on the radially innermost side 99 of ring 36 than on its radially outermost side 100. Also, while there are three tabs in the preferred embodiment, other numbers of tabs may be feasible provided that assembly of the bearing ring with the bearing insert is not made unduly difficult and operation of the joint is not otherwise compromised.

Use of the acetabular endoprosthesis 10 is facilitated by preassembly of the components into two subassemblies: a bearing subassembly comprising the bearing insert with the bearing ring installed in place, and an acetabular shell subassembly comprising the outer shell 10 with the locking ring installed in place. Both subassemblies could be prepackaged as such in various sizes in sterile condition. Thereafter, assembly of the two subassemblies during an operation merely requires only two steps: first, inserting the femoral head into the bearing subassembly and second, inserting the bearing subassembly into the acetabular shell subassembly. The first step results in the bearing ring expanding (primarily) through apertures 84 and 86 to enable head 16 to pass into the socket of the bearing insert. The ring will close up to capture the head and form the bottom part of the socket. Insertion of the bearing subassembly into the acetabular shell subassembly results in the expansion of locking ring 34 until the bearing insert is fully inserted, at which point ring 34 will engage slot 64. The bearing subassembly may be disassembled when desired by expanding the ends of ring 34 to enable the two subassemblies to be pulled apart.

It will be understood that when assembled and in use, the invention causes the forces exerted upon bearing ring 36 to be directed to an area on the inner surface of shell 30 that is distal from open end 43 and rim 42—both directly through ring 36 because of the contiguous relationship between the outer surface of the tabs and the inner surface of the shell, and indirectly through ring 36, via that portion of bearing insert 36 lying intermediate the tabs, to the shell. Even in extreme positions such as when shell 30 might rotate toward varus, the forces exerted upon bearing ring 36 will be transmitted to and supported by an area on the inner surface of the shell distal to the rim.

While the preferred embodiment has been disclosed in terms of a ball-and-socket joint, whether mechanical or biomechanical, it will be understood that the principles of the invention are equally applicable to other types of articulating surfaces. For example, while the socket of the preferred embodiment has a spherical chamber to receive a spherical head, chambers of other shapes could be used in conjunction with appropriately shaped heads if different ranges of motion are desired. For example, a cylindrical chamber may be provided in a bearing insert in conjunction with a cylindrical head which could be rotatable about the axis of the head in only one dimension. In such an embodiment, the bearing ring could be other than circular, it being understood that the bearing ring should be shaped to fit within the particular bearing insert.

It will be understood by those skilled in the art that numerous modifications and improvements may be made to the preferred embodiment of the invention disclosed herein without departing from the spirit and scope thereof.

What is claimed is:

1. An implantable prosthetic socket for use with an associated component having a head, said socket comprising:

an outer cup-shaped shell having an inner surface, an open end and a first peripheral groove formed on its inner surface proximate its open end and an access aperture extending through said shell and said first groove to allow access to said groove from the exterior of said shell;

a cup-shaped bearing insert having a body wall, inner and outer surfaces and an open end, said bearing insert adapted for substantially mateable engagement within said outer shell and having a socket chamber for receiving said head, the wall of said insert having a second peripheral groove on its outer surface proximate the open end of said insert and a plurality of peripherally spaced apertures axially spaced from said second groove;

a split, insert-retaining ring having two ends adjacent a split in the ring, said insert retaining ring adapted to fit within said first and second grooves, said insert-retaining ring provided with grasping means adjacent the two ends, said grasping means being accessible through said access aperture from the exterior of said outer shell; and a split, head-retaining bearing ring having a split therein and being retained within said spaced apertures, said bearing ring being sufficiently expandable, when said bearing insert is not within said outer shell, to enable said head to be inserted past said bearing ring into the socket chamber of said bearing insert, said bearing ring having predetermined portions thereof conforming to and contiguous with the inner surface of said outer shell such that expansion of said bearing ring is opposed by said outer shell.

2. An implantable prosthetic socket according to claim 1 wherein said annularly spaced apertures are situated in a plane substantially perpendicular to an axis of said bearing insert.

3. An implantable prosthetic socket according to claim 1 wherein the inner surface of said outer shell and the inner surface of said bearing surface proximate said space apertures are circular and wherein said bearing ring further comprises:

a plurality of radially outwardly extending tabs, each of said tabs having a radially outermost surface of predetermined arcuate length, the radially outermost surfaces of each of said tabs being positioned at a diameter substantially equal to that of the inner surface of said outer shell when said bearing ring is in a normal, relaxed condition, the radially outwardly facing surface of said ring intermediate said tabs is at a diameter substantially equal to that of the inner surface of said bearing insert when said bearing ring is in said normal, relaxed condition.

4. An implantable prosthetic socket according to claim 1 wherein the split in said bearing ring has an arcuate gap that is smaller on its most radially inward side than on its most radially outward side.

5. An implantable prosthetic socket according to claim 3 wherein said bearing insert is provided with an annular bearing ring-retaining groove on its interior surface, said groove adapted to receive therein predetermined portions of the radially outwardly facing surface of said bearing ring intermediate said tabs.

6. An implantable prosthetic socket according to claim 3 wherein one of said annularly spaced apertures is provided with a keyway and wherein one of said tabs is provided with a key mateable with said keyway.

7. An implantable prosthetic socket according to claim 6 wherein said keyed tab comprises:

a first arcuate body portion having a first predetermined arcuate length; and a second arcuate key portion axially contiguous to said first arcuate portion and having a second predetermined arcuate length smaller than said first arcuate length.

8. An implantable prosthetic socket comprising an outer shell adapted to be received within a bone cavity, a bearing insert disposed within the outer shell and defining a cavity for receiving a head to be coupled with the prosthetic socket, a first means cooperating with the outer shell and the bearing insert to oppose separation therebetween, and a second means spaced from the first means and contiguously cooperating with the head, bearing insert and outer shell to oppose withdrawal of the head from the bearing insert, wherein said second means is an annular ring and wherein the bearing insert defines a slot to carry said annular ring in spaced relation to the first means, wherein the slot extends through the bearing insert at selected locations and is spaced from the outer shell at the other locations.

9. An implantable prosthetic socket for being coupled to an associated head comprising:

an outer shell having an interior surface defining an open end;

a bearing insert having an interior and being adapted for substantially mateable engagement within said outer shell, the interior of said bearing insert providing a top portion of a socket chamber for receiving said head;

means carried by said outer shell for retaining said bearing insert within said shell;

a split bearing ring retained by said bearing insert to form a bottom portion of said socket chamber, said bearing ring being simultaneously contiguous to said head, the interior of said bearing insert and said interior of the outer shell, the contiguity with said outer shell being along arcuately spaced areas on the inner surface of said outer shell, said areas being spaced from the open end of the outer shell.

10. An implantable prosthetic socket according to claim 9 wherein said retaining means comprises annular split ring and groove means to selectively engage the outer surface of said bearing insert to the inner surface of said outer shell and wherein said outer shell is provided with an access aperture therethrough to enable access to said split ring.

11. An implantable prosthetic socket according to claim 9 wherein an annular portion of said bearing insert is contiguous to the interior of said outer shell along a first annular area proximate the open end thereof and wherein said bearing ring is contiguous to the interior of said outer shell along a second annular area spaced from said open end.

12. A prosthetic socket comprising an outer shell, a bearing insert disposed within the outer shell and defining a cavity for receiving a head to be coupled with the prosthetic socket, a first means cooperating with the outer shell and the bearing insert to oppose separation therebetween, and a second means spaced from the first means and contiguously cooperating with the head, bearing insert and outer shell to oppose withdrawal of the head from the bearing insert, wherein said second means is an annular ring and wherein the bearing insert defines a slot to carry said annular ring in space relation to the first means, wherein the slot extends through the bearing insert at selected locations and is spaced from the outer shell at the other locations.

* * * * *